United States Patent [19]

Fehr et al.

[11] Patent Number: 5,114,915
[45] Date of Patent: May 19, 1992

[54] DECALIN KETONES, THEIR USE IN PERFUMERY AND PROCESS FOR THE PREPARATION THEREOF

[75] Inventors: Charles Fehr, Versoix; José Galindo, Les Avanchets; Olivier Guntern, Geneva, all of Switzerland

[73] Assignee: Firmenich SA, Geneva, Switzerland

[21] Appl. No.: 721,747

[22] Filed: Jun. 26, 1991

[30] Foreign Application Priority Data

Jul. 9, 1990 [CH] Switzerland .................. 2283/90

[51] Int. Cl.⁵ .............................................. A61K 7/46
[52] U.S. Cl. .................................... 512/15; 252/174.11; 252/8.6; 424/65
[58] Field of Search ............... 512/15; 252/174.11.8.6; 424/65

[56] References Cited

U.S. PATENT DOCUMENTS

| | | | |
|---|---|---|---|
| 3,072,709 | 1/1963 | Saucy | 512/15 |
| 3,932,515 | 1/1976 | Shaffer et al. | 512/15 |
| 3,937,083 | 12/1975 | Hall et al. | 512/15 |
| 4,387,048 | 6/1983 | Yoshida | 512/15 |

FOREIGN PATENT DOCUMENTS 777055 11/1980 U.S.S.R. ...................... 512/15

OTHER PUBLICATIONS

Banerjee et al., Tetrahedron, vol. 37, p. 2749 (1981).

*Primary Examiner*—James H. Reamer
*Attorney, Agent, or Firm*—Pennie & Edmonds

[57] ABSTRACT

The decalin ketones of formula

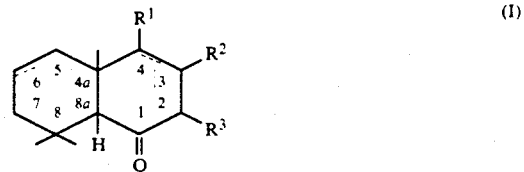

(I)

having a single or double bond in one of the positions indicated by the dotted lines, or two double bonds in positions 2 and 5 or 3 and 5 such as indicated by the dotted lines, and wherein symbols $R^1$, $R^2$ and $R^3$ represent a hydrogen atom or a methyl radical, are useful as perfuming ingredients for the preparation of perfuming compositions and perfumed articles, to which they impart woody-amber odor notes.

A process for the preparation of these ketones is also disclosed.

12 Claims, No Drawings

DECALIN KETONES, THEIR USE IN PERFUMERY AND PROCESS FOR THE PREPARATION THEREOF

BRIEF SUMMARY AND BACKGROUND OF THE INVENTION

The present invention relates to the perfume industry. It concerns more particularly decalin ketones of formula

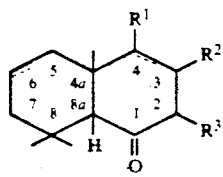

having a single or double bond in one of the positions indicated by the dotted lines, or two double bonds in positions 2 and 5 or 3 and 5 such as indicated by the dotted lines, and wherein symbols $R^1$, $R^2$ and $R^3$ represent a hydrogen atom or a methyl radical, with the exclusion of perhydro-4a,8,8-trimethyl-1-trans-naphthalenone as well as a process for their preparation.

There are many fragrant compounds with a decalin structure known to this day. In particular, a variety of decalin ketones having a more or less similar structure to that of ketones (I) are described in the prior art. G. Ohloff, for example, has described in a review article the odor properties of quite a few of these known compounds and analyzed their properties in the context of a wider study of structure-activity relationships in compounds which develop ambergris-type odor notes [see Fragrance Chemistry: The Sense of Smell, page 535, ed. E. T. Theimer, AP, USA (1982) and references therein].

The majority of these prior art decalin ketones, whose structure is analogous or homologous to that of compounds (I) according to the invention, posses the carbonyl group in a less encumbered ring position and-/or in a position further away from the dimethyl group than in formula (I). This is a result of the fact that, up until now, there were no processes available allowing the industrial preparation of pure decalin ketones of formula (I).

Amongst the ketones of formula (I), only perhydro-4a,8,8-trimethyl-1-trans-naphthalenone, having the formula

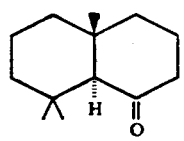

has been described in the prior art, namely by G. Ohloff [ref. cited]. However, the compound disclosed by this author was obviously not obtained in a pure state, since its odor, described as strongly resinous, varnish-like with a musty undertone, is said to be partly due to the olfactive contribution of an analogous ketone of formula

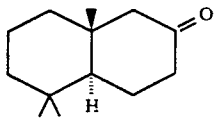

On the other hand, A. K. Banerjee et al. [see Tetrahedron 37, 2749 (1981) and J. Chem. Soc. Perkin Trans. I 1982, 2547] described the preparation of ketone (A) and its use in the synthesis of the following decalin ketones:

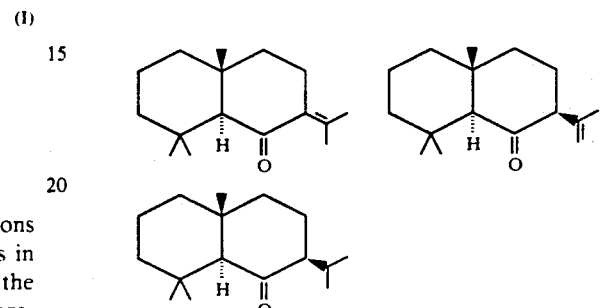

According to these authors, the latter ketones can only be obtained in good yield following an elaborate multi-step process, presenting only an academic interest. In addition, the starting ketone of formula (A) is obtained by means of a process having at least four steps, one of said steps being a reaction of hydroboration-oxidation of an octalin which, for safety reasons, cannot be applied industrially. Likewise, the preparation of said octalin involves reactions which are unsuitable for an industrial synthesis of this compound.

Finally, the above-cited prior art process for the preparation of ketone (A) does not allow the preparation of unsaturated ketones of formula (I) or, at least, it requires further steps which would render the synthesis of these compounds even less adapted to industrial exploitation.

It should be mentioned that Banerjee et al. described only the synthesis of the above-cited compounds and did not suggest any useful application, from an olfactive point of view, of said compounds.

THE INVENTION

It has now been discovered that not only prior known ketone (A), but also other formula (I) saturated or unsaturated decalin ketones could be obtained in good yield and in a straightforward manner thanks to a new process which is an object of the present invention and which resorts to reactions which can be safely and efficiently scaled-up to industrial conditions.

In addition, we have also discovered unexpectedly that the decalin ketones of formula (I) defined above possess very useful odor properties, distinct from those of the prior known decalin ketones. In fact, although the presently disclosed decalin ketones (I) retain the amber-woody character which seems to be typical of this type of compounds [see G. Ohloff, cited reference], they develop entirely surprising and unique odors, wherein the amber-woody note can be accompanied by floral notes reminiscent of the odor of damascones. This combination of odor characters is quite unknown in this type of compounds. Furthermore, depending on the specific nature of compound (I), its odor may still possess other olfactive nuances which render the use of these compounds in perfumery particularly varied.

It has also been noted that the odor character of different isomeric forms of a same formula (I) structure is also distinct. In fact, if one ignores the particular orientation of substituents $R^1$, $R^2$ or $R^3$, the compounds of the present invention can present themselves in two isomeric forms, resulting from the configuration of the methyl group in position 4a of the naphthalenic ring which can be trans or cis relative to the hydrogen atom in position 8a. It has been observed that the trans-configuration isomers represented by the formula

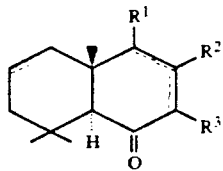

wherein the dotted lines and symbols $R^1$, $R^2$ and $R^3$ have the meaning indicated in formula (I), possess the most useful odor notes and are, therefore, preferred compounds according to the invention. Thus several compounds (I) having this trans- configuration are preferred compounds according to the invention.

For example, one such compound is 4a,5,6,7,8,8a-hexahydro-4a,8,8-trimethyl-1(4H)-trans-naphthalenone possesses a woody, damascone-like odor, with an elegant camphor side note. Its base note is reminiscent of the odor of para-tert-butylcyclohexanol, with a character resembling that of geosmin [see U.S. Pat. No. 4,248,742], and which is also amber-earthy.

On the other hand, 4a,5,6,7,8,8a-hexahydro-3,4a,8,8a-tetramethyl-1(4H)-trans-naphthalenone, also preferred according to the invention, develops a amber-woody note less powerful than that of its homologue above-mentioned, but possessing a clearer powdery, ionone- and damascone-like character.

A third preferred compound of the invention is perhydro-4a,8,8-trimethyl-1-trans-naphthalenone which possesses the same earthy, p-tert-butylcyclohexanol-like odor of the compound first mentioned above, but which develops a more ambery, slightly cashmeran and camphor note than the latter, with a very interesting patchouli character.

This variety of olfactive nuances can also be observed in the other compounds (I) according to the invention, the odor properties of which are described in detail in the preparation examples presented further on.

Thanks to their odor properties, the compounds of formula (I) or (Ia) according to the invention can be advantageously used both in fine and functional perfumery, for the preparation of perfuming compositions and perfumed articles. Amongst the latter, one can cite perfumes and colognes, soaps, shower or bath gels, shampoos and other hair-care products, cosmetic preparations and body deodorants. They can also be used for perfuming detergents, fabric softeners or household products.

The concentrations in which the compounds of the invention can be used to provide the desired perfuming ingredients vary in a wide range of values. It is quite well-known that these concentrations are a function of the conditions of use, i.e., they can vary depending on whether the compound is used alone or in admixture with other ingredients, solvents or adjuvants currently used in perfumery, as well as of the desired perfumed effect. Whenever, as is usual, the compounds (I) are used in admixture with other co-ingredients, their concentration will also depend on the nature of the latter.

Concentrations of the order of 1 to 5%, say 10 or even 20% by weight of compound (I), relative to the weight of the composition in which it is incorporated, can be cited by way of example. These values can be distinctly lower when compound (I) is used for perfuming the varied consumer articles mentioned above.

As it has been cited before, it is also an object of the present invention to provide a process for the preparation of the decalin ketones of formula

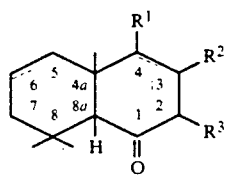

having a single or double bond in one of the positions indicated by the dotted lines, or two double bonds in positions 2 and 5 or 3 and 5 such as indicated by the dotted lines, and wherein symbols $R^1$, $R^2$ and $R^3$ stand for hydrogen or a methyl radical, which process comprises the following steps:

a) the thermal treatment of a compound of formula

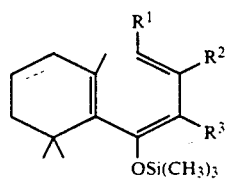

wherein the dotted line indicates the location of a single or double bond and symbols $R^1$, $R^2$ and $R^3$ are defined as in formula (I), followed by an acidic treatment of the reaction product thus obtained and the separation of a compound of formula

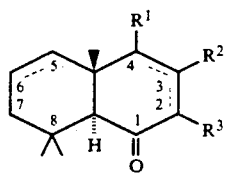

wherein symbols $R^1$, $R^2$ and $R^3$ have the meaning indicated in formula (I) and the dotted lines indicate the location of a single or double bond in position 5 and of a double bond in position 2 or 3 of the naphthalene ring;

b) if necessary, the epimerisation, according to generally known methods, of said compound of formula (Ia) defined in a) to yield its cis-configuration isomer of formula

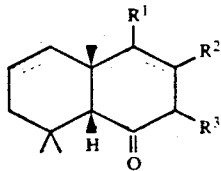

(Ib)

wherein the dotted lines and symbols $R^1$, $R^2$ and $R^3$ have the meaning indicated in formula (Ia); and c) if necessary, the selective reduction, in a generally known manner, of said compound of formula (Ia), respectively of formula (Ib), to obtain a compound of formula

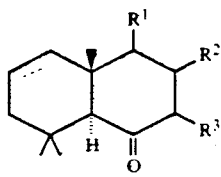

(I'a)

respectively of formula

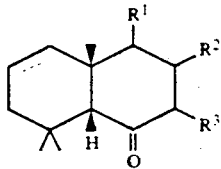

(I'b)

wherein the dotted line indicates the location of a single or double bond and symbols $R^1$, $R^2$ and $R^3$ have the meaning indicated above.

The main step of the process according to the invention is an electrocyclic ring closing reaction through thermal treatment of the compound of formula (II) in an inert organic solvent. This thermal treatment can be a pyrolysis reaction carried out according to current techniques. Typically, a solution of the product to be submitted to pyrolysis, in an inert solvent, is injected at one end of a quartz column previously heated to a predetermined temperature. The operation can be carried out under nitrogen or reduced pressure and the pyrolysate vapors are condensed in a trap cooled to a very low temperature by means of an appropriate cooling mixture. The pyrolysis temperature can vary in a relatively wide range of values, for example 300° to 400° C. Preferably, the reaction temperature should not exceed 400° C. so as to avoid formation of undesirable by-products. According to a preferred embodiment of the process of the invention, the reaction temperature is around 365° C. Nevertheless, this temperature is a function of the length of the quartz column and is particularly dependent on the applied pressure. The man in the art is able to adapt these parameters, as well as others such as the pyrolysis duration, so as to obtain a good yield in the desired final product.

The condensed pyrolysate, containing silylated ethers, is then treated in acidic medium to remove the labile groups, and the thus treated mixture is purified by means of the usual techniques such as fractional distillation, chromatography and crystallization, to yield the compound of formula (Ia) above-defined.

Alternatively, the thermal treatment of compound (II) can be carried out at a lower temperature in a closed autoclave and in solution in an inert organic solvent. Specific reaction conditions are described in detail in the examples described further on.

The starting products of formula (II) can be obtained from esters or ketones commercially available, according to two alternative processes represented in the following scheme and using analogous methods to those described by C. Fehr et al. in Helv. Chim. Acta 69, 228 (1986) and 70, 1745 (1987):

SCHEME I

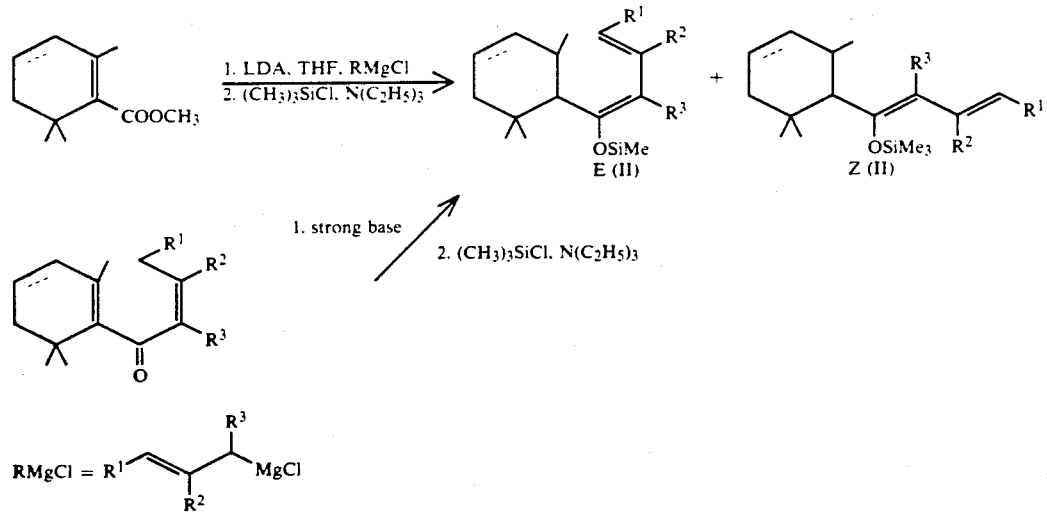

Me = $CH_3$
LDA = lithiumdiisopropylamine
THF = tetrahydrofuran

The first method, starting from the ester represented, is a Grignard reaction carried out in a basic medium, followed by silylation of the resulting enol. The reaction product is a mixture rich in the desired E(II) isomer, the cyclization of which, followed by an acidic treatment intended for removing the labile group, makes it possible to obtain the transconfiguration decalin ketone (Ia), as previously mentioned.

The second process comprises the deprotonation, by means of a strong base, of the ketone represented above, followed by silylation of the resulting enolate. The reaction's diastereoselectivity can be precisely controlled by an appropriate choice of the deprotonating base, as it emerges from the preparation examples presented further on, wherein the specific reaction conditions are disclosed in detail.

According to the process of the invention, the decalin ketones of formula (Ia), wherein symbols $R^1$, $R^2$ and $R^3$ have the meaning indicated in formula (I) and the dotted lines indicate the location of a single or double bond in position 5 and of a double bond in position 2 or 3 of the naphthalene ring, obtained in the preceding reactions, can be converted into their cis-configuration isomers of formula (Ib) by means of conventional type epimerisation reactions.

On the other hand, the above-mentioned cis- or trans-configuration unsaturated ketones can be subjected to selective reduction reactions to provide the cis- or trans-configuration ketones of formula (I'a) and (I'b) previously defined. These are current type reactions such as hydrogenations or reductions carried out with the usual reducing agents, for example, an alkali metal, lithium aluminium hydride or a trialkyl tin hydride [see, for example. H. G. Kuivila et al., J. Amer. Chem. Soc. 83, 1246 (1961) and H. R. Wolf et al. Helv. Chim. Acta 56, 1062 (1973)].

The specific conditions of such reactions are described in detail in the preparation examples presented further on.

The invention will now be described in further detail by way of the preparation examples presented hereinafter, wherein the temperatures are indicated in degrees centigrade and the abbreviations have the usual meaning in the art.

The invention will also be illustrated by way of application examples in perfumery.

EXAMPLE 1

Preparation of
4a,5,6,7,8,8a-hexahydro-4a,8,8-trimethyl-1(4H)-trans-naphthalenone 82.0 G of 1,3,3-trimethyl-2-[1-(trimethylsilyloxy)-1,3-butadienyl]-1-cyclohexene (11:1 = E/Z mixture; 95% chromatographically pure; 295 mmol) in cyclohexane (400 ml) were carried at a speed of 0.8 ml/min through a 4 m quartz column previously heated to 365° and maintained under a constant flow of nitrogen (0.8 ml/min). The pyrolysate (78.0 g) was concentrated in a vessel equipped with a dry ice condenser. The resulting product, which consisted of a mixture containing 1,2,3,4,4a,5-hexahydro-1,1,4a-trimethyl-8-(trimethylsilyloxy)-naphthalene, 1,2,3,4,4a8a-hexahydro-1,1,4a-trimethyl-8-(trimethylsilyloxy)-trans-naphthalene, 1,2,3,4,5,6-hexahydro-1,1,4a,6-tetramethyl-8-(trimethylsilyloxy)-naphthalene and starting product, was dissolved in THF (400 ml), treated with 5% HCl (10 ml) and stirred at 20° for 1 h. After fractional distillation (55°/6.7 Pa) and crystallization (petroleum ether/−78°), 18.2 g of the desired naphthalenone (32% yield) were obtained. The mother waters were purified by chromatography ($SiO_2$, cyclohexane/ethyl acetate = 98:2) and crystallization to give 6.0 g (11% yield) of the same naphthalenone. Other less pure distilled fractions and the remaining mother waters contained ∼16 g (29% yield) of the desired product.

IR: 2920, 1675, 1460, 1380, 1225, 1125 $cm^{-1}$.

NMR($^1$H, 360 MHz): 1.04(s, 3H); 1.14(s, 3H); 1.16(s, 3H); 1.17–1.25(m, 1H); 1.35–1.49(m, 3H); 1.53–1.71(m, 2H); 2.09(dd, J = 18, 6.5 Hz, 1H); 2.19(s, 1H); 2.33(broad d, J = 18 Hz, 1H); 5.89(dd, J = 10, 3.5 Hz, 1H); 6.68(ddd, J = 10, 6.5, 2.5 Hz, 1H) δ ppm.

NMR($^{13}$C): 18.2(t); 20.4(q); 21.3(q); 32.1(s); 33.3(q); 39.1(s); 41.7(t); 43.6(t); 46.4(t); 62.5(d); 130.9(d); 144.5(d); 200.7(s) δ ppm.

MS: 192(20, $M^+$), 177(7), 149(8), 121(16), 109(100), 81(11), 68(13), 55(16), 41(42).

Odor note: described in the introduction.

The starting 1,3,3-trimethyl-2-[1-(trimethylsilyloxy)-1,3-butadienyl]-1-cyclohexene was prepared as follows:

a) Starting from methyl β-cyclogeranate

A solution of butyllithium in hexane (118 ml, 1.40N, 164.8 mmol) was added at a temperature of between −10° and 0° to a stirred solution of diisopropylamine (17.20 g, 24.3 ml, 170.0 mmol) in THF (120 ml). Once the addition was completed, the yellow solution was treated with an allylmagnesium chloride solution in THF (119.0 ml, 1.38N, 164.6 mmol) at 20°, and methyl β-cyclogeranate (20.0 g, 109.8 mmol) was added to the resulting blue-grey solution at 35°–40°. The resulting yellow mixture was stirred at the same temperature for 1 h, cooled to −30° and treated with ($C_2H_5$)$_3$N (22.2 g, 30.4 ml, 219.6 mmol) and ($CH_3$)$_3$SiCl (35.6 g, 41.4 ml, 329.4 mmol). The cooling bath was removed and stirring was kept for 2 h at 20°. The yellow mixture was treated with a saturated solution of $NaHCO_3$/ice/petroleum ether and extracted. The organic layer was washed with water and saturated NaCl, dried over $Na_2SO_4$, evaporated and distilled (55°–60°/6.7 Pa). 24.4 G of 1,3,3-trimethyl-2-[1-(trimethylsilyloxy)-1,3-butadienyl]-1-cyclohexene were obtained, in the form of an E/Z = 3:1 isomer mixture (95% pure, 80% yield). IR: 2920, 1620, 1580, 1455, 1245, 1205, 1160, 1060 $cm^{-1}$.

Isomer E

NMR($^1$H, 360 MHz): 0.24(s, 9H); 0.96(s, 3H); 1.11(s, 3H); 1.44(m, 2H); 1.59(s, 3H); 1.60–1.74(m, 2H); 1.92–2.07(m, 2H); 4.72(dd, J = 10, 2 Hz, 1H); 4.93(dd, J = 17, 2 Hz, 1H); 5.49(d, J = 10 Hz, 1H); 6.05(ddd, J = 17, 10, 10 Hz, 1H) δ ppm.

Pos. NOE between 0.24(ν) and 5.49 δ ppm [see T. H. Keller et al., J. Org. Chem. 52, 1870 (1987)].

NMR($^{13}$C, 360 MHz): 0.5(q); 19.0(t); 2.14(q); 28.7(q); 29.6(q); 31.7(t); 33.9(s); 39.6(t); 110.7(t); 112.1(d); 132.0(s); 135.1(d); 154.1(s) δ ppm.

MS: 264(3, $M^+$), 249(6), 194(9), 179(34), 105(12), 91(14), 75(35), 73(100), 55(10), 45(15).

Isomer Z

NMR($^1$H, 360 MHz): relevant peaks: 0.17(s, 9H); 170(s, 3H); 4.84(dd, J = 10, 2 Hz, 1H); 4.99(dd, J = 17, 2 Hz, 1H); 5.16(d, J = 10 Hz, 1H); 6.63(ddd, J = 17, 10, 10 Hz, 1H) δ ppm.

NMR($^{13}$C, 360 MHz): detected peaks: 0.9(q); 22.2(q); 29.4(q); 31.9(t); 39.8(t); 111.7(t); 115.3(d); 132.0(d) δ ppm.

MS: 264(3, $M^+$), 249(6), 194(10), 179(38), 105(12), 91(15), 75(35), 73(100), 55(11), 45(15).

b) Starting from β-damascone

A β-damascone (5.0 g, 26.0 mmol) solution in THF (20 ml) was added dropwise to a cooled (−75°) solution of NaN[Si(CH₃)₃]₂ (Aldrich, 1.0M in THF, 30.0 ml, 30.0 mmol) in THF (30 ml). The deprotonation was completed in 15 min. At the same temperature (CH₃)₃SiCl (3.40 g, 3.95 ml, 31.4 mmol) was added over 2 min. After 1 h, the clear yellow solution was treated with N(C₂H₅)₃ (2.62 g, 3.60 ml, 26.0 mmol), saturated aqueous NaHCO₃/ice/petroleum ether and extracted to give, after bulb-to-bulb distillation (bath temperature 80°/8 Pa), 6.01 g of 1,3,3-trimethyl-2-[1-(trimethylsilyloxy)-1,3-butadienyl]-1-cyclohexene in the form of an E/Z=11:1 isomer mixture (88% yield).

By repeating this process with LiN[Si(CH₃)₃]₂, respectively KN[Si(CH₃)₃]₂, instead of NaN[Si(CH₃)₃]₂, isomer mixtures of E/Z=7:1 (93% yield), respectively E/Z=8:1, were obtained, with deprotonation times of about 20 h, respectively 1 h.

The products thus obtained had the same analytical data as the mixture obtained in a).

EXAMPLE 2

Preparation of 4a,5,6,7,8,8a-hexahydro-4a,8,8-trimethyl-1(4H)-cis-naphthalenone

This compound was obtained by epimerization of its trans isomer prepared in example 1. The trans-decalin (500 mg, 2.6 mmol) was heated to reflux in toluene (25 ml), in the presence of hydrated p-toluenesulfonic acid (p-TsOH.H₂O, 495 mg, 2.6 mmol), for 40 h. The reaction mixture, once cooled, was poured on H₂O and extracted with ether. The organic layer was washed twice with NaHCO₃ and once with brine, then dried and evaporated (460 mg). The resulting product was purified on a silica column, using a mixture of 1:1 hexane/methylene chloride, and then methylene chloride as eluting agent. After distillation, 332 mg of the desired product (66% yield) were obtained.

M.p. 70°–78.5°.

IR: 2900, 1640, 1450, 1370, 1240, 1130 cm⁻¹.

NMR(¹H, 360 MHz): 0.88(s, 3H); 0.97(s, 3H); 0.98(s, 3H); 1.14–1.26(m, 2H); 1.39–1.71(m, 4H); 1.82(s, 1H); 1.84(dd, J=20, 6 Hz, 1H); 2.71(broad d, J=20 Hz, 1H); 6.01(dd, J=10, 2.5 Hz, 1H); 6.82(m, 1H) δ ppm.

NMR(¹³C): 18.7(t); 22.2(q); 31.6(q); 32.8(q); 34.0(s); 35.2(s); 35.6(t); 39.4(t); 41.5(t); 63.3(s); 130.1(d); 147.7(d); 202.2(s) δ ppm.

MS: 192(6, M⁺), 177(2), 149(4), 121(7), 109(100), 97(4), 81(6), 79(6), 67(5), 55(4), 41(6).

EXAMPLE 3

Preparation of 4a,5,6,7,8,8a-hexahydro-3,4a,8,8-tetramethyl-1(4H)-trans-naphthalenone 55.5 G of 1,3,3-trimethyl-2-[3-methyl-1-(trimethylsilyloxy)-1,3-butadienyl]-1-cyclohexene (E/Z=2.2:1 isomer mixture; 61% chromatographically pure; 122 mmol) in 400 ml of hexane were pyrolysed as described in example 1. The pyrolysate was dissolved in THF (250 ml) and treated with aqueous HCl (50 ml H₂O+2.8 ml concentrated HCl). After 45 min, water and petroleum ether were added thereto. The organic layer was washed (H₂O, then saturated NaCl) dried over Na₂SO₄, evaporated (33.5 g) and distilled (70°/6.7 Pa) to give 30.6 g of a mixture containing 54% of the desired naphthalenone, as well as starting product. Fractional distillation of this mixture provided fractions containing the starting cyclohexene (9.0 g, b.p. 53°–60°/6.7 Pa, 27% estimated yield) and fractions rich in the above-mentioned naphthalenone (17.5 g, 70% yield). Crystallization (petroleum ether/−30°) of the purest distilled fractions (14.2 g) gave the said naphthalenone in a crystalline form (13.9 g, 55% yield).

IR: 2920, 1665, 1465, 1435, 1375, 1360, 1225, 1155 cm⁻¹.

NMR(¹H, 360 MHz): 1.00(s, 3H); 1.14(s, 3H); 1.15(s, 3H); 1.10–1.71(m, 6H); 1.87(s, 3H); 1.93(d, J=18 Hz, 1H);2.07(s, 1H); 2.31(broad d, J=18 Hz, 1H); 5.74(broad s, 1H) δ ppm.

NMR(¹³C, 360 MHz): 18.3(t); 20.4(q); 21.3(q); 23.8(q); 32.1(s); 33.4(q); 38.6(s); 41.6(t); 43.8(t); 51.8(t); 61.6(d); 127.4(d); 155.7(s); 200.3(s) δ ppm.

MS: 206(8, M⁺), 191(7), 163(5), 135(9), 123(100), 109(20), 82(23), 41(12).

Odor note: described in the introduction.

The starting 1,3,3-trimethyl-2-[3-methyl-1-(trimethylsilyloxy)-1,3-butadienyl]-1-cyclohexene was prepared as follows:

a) Starting from methyl β-cyclogeranate

A solution of LDA (lithium diisopropylamine; see example 1a); 415 mmol) in THF/hexane (~650 ml) was treated with methylallyl magnesium chloride in THF (248 ml, 1.67N, 415 mmol). Methyl β-cyclogeranate (50.0 g, 275 mmol) in THF (50 ml) was added at 40° to the thus obtained grey-brown solution. The mixture was stirred at 35°–40° for 2 h and at 20° for 15 h. The cooled reaction mixture (−30°) was treated with (CH₃)₃SiCl (88.5 g, 103.0 ml, 825 mmol). After removing the cooling bath, stirring was continued for 2 h at 20°. Following the treatment described in example 1a) [27.8 g of (C₂H₅)₃N, 275 mmol)], extraction and distillation (62°–68°/6.7 Pa), 68.8 g of a mixture (61% pure) of isomers of the desired cyclohexene, in the proportions E/Z=2.2:1 (55% yield), were obtained.

Analytical data:

(E)-1,3,3-trimethyl-2-[3-methyl-1-(trimethylsilyloxy)-1,3-butadienyl]-1-cyclohexene NMR(¹H, 360 MHz): 5.08(s, vinyl H) δ ppm.

(Z)-1,3,3-trimethyl-2-[3-methyl-1-(trimethylsilyloxy)-1,3-butadienyl]-1-cyclohexene NMR(¹H, 360 MHz): 4.88(s, vinyl H) δ ppm.
NOE(ν0.15)→pos. 1.71; 1.99 δ ppm.
NOE(ν1.71)→pos. 0.15; 4.88 δ ppm.
NOE(ν1.99)→pos. 0.15; 4.73; 4.88 δ ppm.

b) Starting from 3-methyl-1-(2,2,5-trimethyl-1-cyclohexenyl)-2-buten-1-one

The same method as described in example 1b) was followed, using 1.0 g of butenone (4.85 mmol) in 50 ml of THF and 5.40 ml (5.40 mmol) of NaN[(CH₃)₃Si]₂ in 20 ml of THF, 0.68 ml (585 mg, 5.40 mmol) of (CH₃)₃SiCl. After stirring for 1 h, and treating as previously described, followed by bulb-to-bulb distillation (bath temperature 85°/8 Pa), 0.94 g (70% yield) of (Z)-1,3,3-trimethyl-2-[3-methyl-1-(trimethylsilyloxy)-1,3-butadienyl]-1-cyclohexene, the analytical data of which were identical to those of the Z isomer obtained in a).

EXAMPLE 4

Preparation of
4a,5,6,7,8,8a-hexahydro-3,4a,8,8-tetramethyl-1(4H)-cis-naphthalenone This compound was obtained by epimerisation of its trans isomer prepared in example 3, following the method described in example 2. After distillation, 294 mg of the desired product were obtained (59% yield).

IR(CDCl$_3$): 2940 (broad), 1650, 1460, 1260, 1180 cm$^{-1}$.

NMR($^1$H, 360 MHz, CDCl$_3$): 0.83(s, 3H); 0.94(s, 3H); 0.99(s, 3H); 1.69(d, J=20 Hz, 1H); 1.75(s, 1H); 1.92(s, 3H); 2.68(d, J=20 Hz, 1H); 5.87(s, 1H) δ ppm.

NMR($^{13}$C, 360 MHz, CDCl$_3$): 16.6(t); 22.1(q); 24.2(q); 31.7(q); 32.8(q); 33.9(s); 34.9(s); 39.3(t); 40.7(t); 41.4(t); 62.1(d); 126.7(d); 158.9(s); 202.2(s) δ ppm.

MS: 206(7, M$^+$), 191(6), 135(8), 123(100), 109(15), 91(5), 82(18), 79(6), 67(6), 55(5), 41(7).

Odor note: amber, dry, powerful, slightly naphthalenic.

EXAMPLE 5

Preparation of
perhydro-4a,8,8-trimethyl-1-trans-naphthalenone

Prepared from the naphthalenone obtained in example 1 (4.00 g, 20.8 mmol) in ethanol (40 ml), by hydrogenation with Pd/C (10%, 100 mg). After 20 min (H$_2$ consumed: 480 ml), the suspension was filtered on Celite ®, concentrated and bulb-to-bulb distilled (85°/13.3 Pa). 39 G (97% yield) of perhydro-4a,8,8-trimethyl-1-trans-naphthalenone were obtained. The analytical data of this product were identical to those published in the cited literature.

Odor note: described in the introduction.

EXAMPLE 6

Preparation of perhydro-3α,4aα,8,8-tetramethyl-1-trans-naphthalenone

Obtained by hydrogenation of the naphthalenone described in example 3 and according to the process described in example 5.

B. p. 90°/5.3 Pa.

IR: 2920, 1710, 1455, 1390, 1380 cm$^{-1}$.

NMR($^1$H, 360 MHz): 0.99(s, 3H); 1.01(s, 3H); 1.02(d, J=7 Hz, 3H); ~1.0-1.2(m, 1H); 1.20(s, 3H); 1.23-1.46(m, 4H); 1.50-1.67(m, 2H); 1.85(dd, J=14,7 Hz, 1H); 1.98(dd, J=16, 7 Hz, 1H); 2.21(s, 1H); 2.33(o, J=7 Hz, 1H); 2.47(dd, J=16, 6.5 Hz, 1H) δ ppm.

NMR($^{13}$C, 360 MHz): 18.7(t); 21.5(q); 22.0(q); 25.4(q); 28.6(d); 32.2(s); 32.9(q); 37.9(s); 43.1(t); 43.3(t); 48.8(t); 50.5(t); 62.6(d); 212.6(s) δ ppm.

MS: 208(7, M$^+$), 193(6), 151(100), 125(23), 123(29), 109(13), 95(13), 81(19), 69(18), 67(16), 55(15), 41(21).

Odor note: woody, amber, weak.

EXAMPLE 7

Preparation of
perhydro-3β,4aα,8,8-tetramethyl-1-trans-naphthalenone

CH$_3$MgBr in ethyl ether (3M, 2.2 ml, 6.6 mmol, Aldrich) was added, at −5° and over 1 min, to a suspension of CuI (50 mg) in ether (10 ml). The green solution was stirred at −5° for 10 min. A solution of the naphthalenone prepared as in example 1 (1.16 g, 6.00 mmol) in ether (10 ml) was then added dropwise. The reaction mixture was stirred for 90 min at −5°, poured over a mixture of saturated NH$_4$Cl/ice and extracted with petroleum ether. The organic layer was washed (H$_2$O, then saturated NaCl), dried over Na$_2$SO$_4$, concentrated (1.10 g) and bulb-to-bulb distilled (100°/10.6 Pa) to give 850 mg of perhydro-3β,4aα,8,8-tetramethyl-1-trans-naphthalenone (96% pure, 65% yield).

IR:2920, 1705, 1455, 1385; 1360, 1225 cm$^{-1}$.

NMR($^1$H, 360 MHz):0.92(s, 3H); 0.96(s, 3H); 0.97(d, J=7 Hz, 3H); ~1.0-1.2(m, 1H); 1.19(s, 3H); ~1.2-1.4(m, 3H); 1.38-1.47(m, 1H); 1.47-1.57(m,2H); 1.57-1.72(m, 1H); 1.96(broad t, J=12 Hz, 1H); 2.04(s, 1H); 2.09(broad m, 1H); 2.28(m,d,J=12 Hz, 1H) δ ppm.

NMR($^{13}$C):18.5(t); 21.2(q); 21.3(q); 22.5(q); 29.9(d); 32.0(s); 32.5(q); 39.6(s); 41.6(t); 43.3(t); 52.2(t); 53.7(t); 64.5(d); 211.7(s) δ ppm.

MS:208(25, M$^+$), 193(19), 165(12), 151(100), 137(10), 125(86), 109(19), 95(23), 81(25), 69(30), 67(23), 55(23), 41(28).

Odor note: woody-amber, weak, slightly acid.

EXAMPLE 8

Preparation of
4a,5,6,7,8,8a-hexahydro-4aα,8,8-trimethyl-1(2H)-trans-naphthalenone This compound was prepared by pyrolysis of 1,3,3-trimethyl-2-[1-(trimethylsilyloxy)-1,3-butadienyl]-1-cyclohexene (E/Z=3:1 mixture; 53 g) according to the process described in example 1. Simple distillation, followed by fractional distillation and treatment with a few drops of concentrated HCl gave, after chromatography on silica column (20 g, cyclohexane/ethyl acetate 98:2), a fraction (147 mg) which contained 53% of the desired naphthalenone. The desired compound was also prepared in a pure state starting from 4a,5,6,7,8,8a-hexahydro-4a,8,8-trimethyl-1(4H)-trans-naphthalenone obtained in example 1, as follows: a solution of this naphthalenone (192 mg, 1.0 mmol) in THF (5 ml) was added dropwise to a cooled solution (−30°) of NaN[(CH$_3$)$_3$Si]$_2$ (Aldrich, 1.0M in THF, 1.10 ml, 1.10 mmol) in THF (3 ml). After 45 min, the mixture was poured on H$_2$O, then extracted with ether/5% aqueous HCl. The organic phase was washed with water and then with an aqueous solution saturated with NaCl, dried on Na$_2$SO$_4$, concentrated and bulb-to-bulb distilled (70°/6.7 Pa). 155 Mg of the desired naphthalenone (81% yield) were obtained.

IR:2920, 1715, 1650, 1460, 1390 cm$^{-1}$.

NMR($^1$H, 360 MHz): 0.98(s, 3H); 1.01(s, 3H); 1.25(s, 3H); 1.08-1.19(m, 1H); 1.25(s, 3H); 1.33-1.72(m, 5H); 2.40(s, 1H); 2.73(broad d, J=21 Hz, 1H); 2.89(dt, J=21, 3.5 Hz, 1H); 5.52(dt, J=8, 3.5 Hz, 1H); 5.63(broad d,J=8 Hz, 1H) δ ppm.

NMR($^{13}$C, 360 MHz): 18.5(t); 21.4(q); 22.0(q); 32.1(s); 32.5(q); 39.4(t); 40.4(s); 42.5(t); 43.0(t); 63.8(d); 120.2(d); 141.8(d); 209.8(s) δ ppm.

MS: 192(70, M$^+$), 177(58), 164(17), 149(27), 135(32), 121(14), 107(32), 93(30), 83(38), 79(66), 67(20), 55(43), 41(100), 39(84).

EXAMPLE 9

Preparation of
4a,7,8,8a-tetrahydro-4a,8,8-trimethyl-1(4H)-trans-naphthalenone 120.5 G (460 mmol) of 2,6,6-trimethyl-1-[1-(trimethylsilyloxy)-1,3-butadienyl]-1,3-cyclohexadiene (E/Z=8:1 mixture) in toluene (100 ml) were heated to 220° in an autoclave (observed pressure: 8×10$^5$ Pa).

After 9 h. the reaction mixture was cooled and concentrated, put in solution in THF (200 ml), treated with 5% HCl (30 ml) and stirred for 1 h at 20°. After fractional distillation (57°/6.7 Pa) and crystallization (petroleum ether/−78°), 12.1 g of the desired naphthalenone were obtained (14% yield).

IR (liq.): 2940, 1680, 1460, 1375, 1285, 1220 cm$^{-1}$.

NMR($^1$H,360MHz): 1.10(s,3H); 1.15(s, 3H); 1.20(s,3H); 1.75(dd,J=17,5 Hz,1H); 1.95(broad d, J=17 Hz, 1H); 2.16(dd,J=18,6 Hz,1H); 2.39(broad d, J=18 Hz, 1H); 2.58(s,1H); 5.45(dd.J=10,2 Hz,1H); 5.55(m,1H); 5.93(dd,J=10, 3.5 Hz,1H); 6.65(m,1H) δ ppm.

NMR($^{13}$C): 20.3(q); 22.6(q); 30.3(s); 30.9(q); 39.9(s); 42.6(t); 44.5(t); 60.4(d); 123.4(d); 131.7(d); 134.8(d); 143.6(d); 200.8(s) δ ppm.

MS: 190(27,M$^+$), 175(24), 157(10), 147(27), 134(28), 122(28), 107(100), 91(55), 83(47), 79(25), 77(25), 69(18), 65(17), 55(20), 41(20), 39(22).

Odor note: woody-camphor, amber, very fenchylic.

The starting 2,6,6-trimethyl-1-[1-(trimethylsilyloxy)-1,3-butadienyl]-1,3-cyclohexadiene was prepared according to the process described in example 1b), starting from β-damascenone (98.9 g, 521 mmol). 120.5 G of the desired product (E/Z=8:1 mixture) were obtained (88% yield).

Isomer E

NMR($^1$H, 360 MHz): 0.24(s, 9H); 1.00(s,3H); 1.08(s,3H); 1.69(s,3H); 1.98(dd, J=18,2 Hz,1H); 2.15(d,J=18 Hz, 1H); 4.76(dd,J=10,2 Hz,1H); 4.99(dd, J=17,2 Hz,1H); 5.54(d,J=10 Hz, 1H); 5.84(m,2H); 6.13(ddd.J=17,10,10 Hz, 1H) δ ppm.

MS: 262(9,M$^+$), 247(17), 219(15), 91(12), 75(19), 73(100), 45(15).

EXAMPLE 10

Preparation of 4a5,6,7,8,8a-hexahydro-2,4a,8,8-tetramethyl-1(4H)-trans-naphthalenone 8.00 G (28.8 mmol) of 1,3,3-trimethyl-2-[2-methyl-1-(trimethylsilyloxy)-1,3-butadienyl]-1-cyclohexene (E/Z=99:1) in toluene (100 ml) were heated at 220° in an autoclave. After 9 h, the reaction mixture was cooled, concentrated, put in solution in THF (20 ml), treated with concentrated HCl (0.5 ml) and stirred for 1 h at 20°. After bulb-to-bulb distillation (100°/13.3 Pa), 4.30 g (yield 72%) of product were obtained, which were purified by cold crystallization (petroleum ether) to give 2.50 g of the desired naphthalenone.

IR (liq.): 2925, 1670, 1455, 1375, 1355 cm$^{-1}$.

NMR($^1$H, 360 MHz): 1.00(s,3H); 1.14(s,3H); 1.17(s,3H); 1.19(m,1H); 1.39(m,3H); 1.59(m,2H); 1.74(broad s,3H); 2.04(dd,J=18,6 Hz,1H); 2.15(s,1H); 2.29(broad d,J=18 Hz,1H); 6.44(broad d,J=6 Hz,1H) δ ppm.

NMR($^{13}$C): 15.9(q); 16.3(t); 20.5(q); 21.4(q); 32.3(s); 33.4(q); 39.4(s); 41.9(t); 43.9(t); 46.4(t); 62.5(d); 136.1(s); 139.4(d); 200.9(s) δ ppm.

MS: 206(17,M$^+$), 123(100), 109(18), 82(45), 41(12).

Odor note: amber-ambrinol, woody, patchouli.

The starting 1,3,3-trimethyl-2-[2-methyl-1-(trimethylsilyloxy)-1,3-butadienyl]-1-cyclohexene was prepared acording to the method described in example 1b), starting from (E)-2-methyl-1-(2,6,6-trimethyl-1-cyclohexen-1-yl)-2-buten-1-one (8.0 g, 38.8 mmol; see process described in U.S. Pat. No. 3,931,326). 8.30 G of the desired product (E/Z=99:1) were obtained (yield 77%).

NMR($^1$H, 360 MHz): 0.16(s,9H); 0.90(s,3H); 1.12(s,3H); 1.44(m,2H); 1.54(s,3H); 1.67(m,2H); 1.75(s,3H); 1.98(m,2H); 4.78(split d,J=10 Hz, 1H); 4.95(split d,J=18 Hz,1H); 6.33(dd,J=18,10 Hz,1H) δ ppm.

EXAMPLE 11

Preparation of perhydro-2α,4aα,8,8-tetramethyl-1-trans-naphthalenone

This compound was prepared according to the method described in example 5, starting from the naphthalenone obtained in example 10 (1.0 g, 4.85 mmol). After bulb-to-bulb distillation (100°/13.3 Pa), 1.00 g (yield 99%) of the title naphthalenone were obtained.

IR (liq.): 2920, 1705, 1450, 1380, 1355 cm$^{-1}$.

NMR($^1$H, 360 MHz): 0.88(s,3H); 0.93(s,3H); 0.98(d,J=6.5 Hz,3H); 1.10(dt, J=14,3.5 Hz,1H); 1.22(s,3H); ~1.25-1.70(m,8H); 1.94(m,1H); 2.09(s,1H); 2.34(h,J=6.5 Hz,1H) δ ppm.

NMR($^{13}$C): 14.6(q); 18.6(t); 20.6(q); 21.6(q); 32.3(t); 32.5(q); 41.2(2s); 41.7(t); 43.5(t); 44.5(t); 46.6(d); 65.3(d); 213.2(s) δ ppm.

MS: 208(8,M$^+$), 193(6), 151(100), 123(18), 109(8), 95(10), 81(13), 67(12), 55(12), 41(14).

Odor note: woody-amber.

EXAMPLE 12

Perfuming Composition for a Masculine Cologne

A base perfuming composition for a masculine cologne was prepared by admixing the following ingredients:

| Ingredients | Parts by weight |
| --- | --- |
| Benzyl acetate | 150 |
| Linalyl acetate | 500 |
| 10%* $C_{10}$ aldehyde | 150 |
| Synthetic bergamot oil | 600 |
| Citral | 500 |
| Lemon essential oil | 1300 |
| Coumarine | 200 |
| Exaltex ®$^{(1)}$ | 500 |
| Bourbon geranium essential oil | 550 |
| Lavandin essential oil | 1000 |
| Lilial ®$^{(2)}$ | 200 |
| Ethyl linalol | 500 |
| Musk ambrette | 500 |
| 10%* Rose oxide | 500 |
| Patchouli essential oil | 850 |
| Petitgrain essential oil | 150 |
| Cedryl acetate | 700 |
| Linalyl propanate | 150 |
| Amyl salicylate | 100 |
| Benzyl salicylate | 400 |
| 10%* Polysantol ®$^{(3)}$ | 500 |
| Vertofix coeur$^{(4)}$ | 700 |
| Total | 10700 |

*in dipropyleneglycol (DIPG).
$^{(1)}$cyclopentadecanolide; origin: Firmenich SA, Geneva, Switzerland.
$^{(2)}$3-(4-tert-butyl-1-phenyl)-2-methylpropanal; origin: L. Givaudan, Geneva, Switzerland.
$^{(3)}$(1'R,E)-3,3-dimethyl-5-(2',2',3'-trimethyl-3'-cyclopenten-1'-yl)-4-penten-2-ol; origin: Firmenich SA, Geneva, Switzerland.
$^{(4)}$origin: International Flavors and Fragrances, USA.

The addition to this base composition of 300 parts by weight of 4a,5,6,7,8,8a-hexahydro-4a,8,8-trimethyl-1(4H)-trans-naphthalenone imparted to the new composition thus obtained a very characteristic amber-woody note and exalted the floral character of the composition.

When 300 parts by weight of 4a,5,6,7,8,8a-hexahydro-3,4a,8,8-tetramethyl-1(4H)-trans-naphthalenone were added to the same base composition, the resulting new composition acquired a less masculine-woody-amber note than that of the preceding novel composition, but it developed a more floral and sweeter odor note.

EXAMPLE 13

Perfuming Composition for a Powder Detergent

A base perfuming composition intended for a powder detergent was prepared by admixing the following ingredients:

| Ingredients | Parts by weight |
|---|---|
| Styrallyl acetate | 1 |
| Carbinol acetate | 3 |
| Hexylcinnamic aldehyde | 20 |
| 10%* Ambrox ®[1] DL | 1 |
| Verdyl acetate | 3 |
| Isononyl acetate | 2 |
| Verdyl propanate | 5 |
| Coumarine | 1 |
| 50%* Bourgeonal[2] | 3 |
| 4-tert-Butyl-cyclohexyl acetate[3] | 15 |
| Fleuramone ®[4] | 1 |
| Cyclomethylene citronellol | 5 |
| Isoraldeine ®[5] 70 P | 3 |
| Lilial ®[6] | 5 |
| Mayol ®[7] | 2 |
| Phenethylol | 6 |
| Amyl salicylate | 3 |
| Tetrahydro muguol[8] | 3 |
| Dimyrcetol | 2 |
| 10%* α-Damascone | 5 |
| Verdox ®[9] | 1 |
| Vertofix coeur[10] | 4 |
| Galaxolide ®[11] 50 | 5 |
| Total | 99 |

*in dipropyleneglycol (DIPG)
[1]racemic tetramethyl perhydronaphthofuran, origin Firmenich SA, Geneva, Switzerland
[2]3-(4-tert-butyl-phenyl)-propanal, origin Naarden Int.
[3]rich in cis-isomer, origin Fermenich SA, Geneva, Switzerland
[4]2-heptyl-1-cyclopentanone, origin International Flavors and Fragrances, USA
[5]iso-methyl ionone, origin 1, Givaudan, Geneva, Switzerland
[6]see example 12
[7]hydroxymethyl isopropyl cyclohexane, origin Firmenich SA, Geneva, Switzerland
[8]isomer mixture, origin International Flavors and Fragrances, USA
[9]2-tert-butyl-1-cyclohexyl acetate, origin International Flavors and Fragrances, USA
[10]see example 12
[11]1,3,4,6,7,8-hexahydro-4,6,6,7,8,8-hexamethyl-cyclopental[9]isochromene, origin International Flavors and Fragrances, USA The addition to this base composition of 1 part by weight of 4a,5,6,7,8,8a-hexahydro-4a,8,8-trimethyl-1(4H)-trans-naphthalenone imparted to the new composition thus obtained a woody and earthy note. In addition, the floral character was clearly reinforced and there was even a new damascone-like odor note which could not be detected in the base composition.

EXAMPLE 14

Perfuming Composition for a Cosmetic Preparation

A base perfuming composition intended for a cosmetic preparation was obtained by admixing the following ingredients:

| Ingredients | Parts by weight |
|---|---|
| Benzyl acetate | 400 |
| Geranyl acetate | 50 |
| Linalyl acetate | 600 |
| Styrallyl acetate | 50 |
| 10%* $C_{11}$ aldehyde | 300 |
| Hexylcinnamic aldehyde | 500 |
| 1%* Phenylacetic aldehyde | 200 |
| Lemon essential oil | 300 |
| Levocitrol | 200 |
| Coumarine | 100 |
| Cyclosal | 100 |
| 1%* Ethylvanillin | 300 |
| Eugenol | 300 |
| Galaxolide ®[1] 50 | 1800 |
| Geraniol | 300 |
| Synthetic geranium | 200 |
| Linalol | 600 |
| Iralia ®[2] | 100 |
| Hedione ®[3] | 300 |
| Patchouli essential oil | 600 |
| Phenethylol | 500 |
| Amyl salicylate | 400 |
| Benzyl salicylate | 600 |
| 10%* Polysantol ®[4] | 200 |
| Natural α-Terpineol | 100 |
| Vertofix coeur[5] | 500 |
| Synthetic Ylang | 200 |
| Total | 9800 |

*in dipropyleneglycol (DIPG)
[1]see example 13
[2]methylionone (isomer mixture), origin Firmenich SA, Geneva, Switzerland
[3]methyl dihydrojasmonate
[4]see example 12
[5]see example 12

The addition to this base composition of the woody-amber-musky type of 200 parts of perhydro-4a,8,8-trimethyl-1-trans-naphthalenone gave a new composition possessing a reinforced woody-patchouli character and a net amber-musky connotation.

What we claim is:

1. A method to confer, improve, enhance or modify the odor properties of a perfuming composition or a perfumed article, which method comprises adding to said composition or article a fragrance effective amount of a decalin ketone of formula

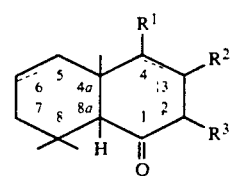

(I)

having a single or double bond in one of the positions indicated by the dotted lines, or two double bonds in positions 2 and 5 or 3 and 5 such as indicated by the dotted lines, and wherein symbols $R^1$, $R^2$ and $R^3$ represent a hydrogen atom or a methyl radical.

2. A method according to claim 1, wherein said decalin ketone is used in its isomeric form of formula

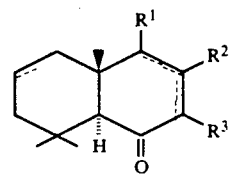

(Ia)

wherein the dotted lines and symbols $R^1$, $R^2$ and $R^3$ are defined as in claim 1.

3. A method according to claim 2 wherein said decalin ketone is perhydro-4a,8,8-trimethyl-1-trans-naphthalenone, 4a,5,6,7,8,8a-hexahydro-4a,8,8-trimethyl-1(4H)-trans-naphthalenone or 4a,5,6,7,8,8a-hexahydro-3,4a,8,8-tetramethyl-1(4H)-trans-naphthalenone.

4. A perfuming composition containing as a perfuming ingredient a decalin ketone of formula (I) or (Ia) as defined in claim 1 or 2.

5. A perfumed article containing as a perfuming ingredient a decalin ketone of formula (I) or (Ia) as defined in claim 1 or 2.

6. A perfumed article according to claim 5, in the form of a perfume or a Cologne, a soap, a shower or bath gel, a shampoo, a body deodorant, a cosmetic preparation, a detergent or a fabric softener or a household product.

7. A composition according to claim 4 wherein said decalin ketone is perhydro-4a,8,8-trimethyl-1-trans-naphthalenone.

8. A composition according to claim 4 wherein said decalin ketone is 4a,5,6,7,8,8a-hexahydro-4a,8,8-trimethyl-1(4H)-trans-naphthalenone.

9. A composition according to claim 4 wherein said decalin ketone is 4a,5,6,7,8,8a-hexahydro-3,4a-8,8-tetramethyl-1(4H)-trans-naphthalenone.

10. An article according to claim 5 wherein said decalin ketone is perhydro-4a,8,8-trimethyl-1-trans-naphthalenone.

11. An article according to claim 5 wherein said decalin ketone is 4a,5,6,7,8,8a-hexahydro-4a,8,8-trimethyl-1(4H)-trans-naphthalenone.

12. An article according to claim 5 wherein said decalin ketone is 4a,5,6,7,8,8a-hexahydro-3,4a-8,8-tetramethyl-1(4H)-/trans-naphthalenone.

* * * * *